US00PP20336P3

(12) United States Plant Patent

Dozier, Jr. et al.

(10) Patent No.: US PP20,336 P3

(45) Date of Patent: Sep. 22, 2009

(54) CHESTNUT PLANT NAMED 'AU ENCORE'

(50) Latin Name: *Castanea seguinii*
Varietal Denomination: AU Encore

(75) Inventors: W. Alfred Dozier, Jr., Opelika, AL (US); Joseph Daniel Norton, Auburn, AL (US); Curtis J. Hansen, Opelika, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/012,017

(22) Filed: Jan. 30, 2008

(65) Prior Publication Data

US 2009/0193548 P1 Jul. 30, 2009

(51) Int. Cl.
*A01H 5/00* (2006.01)

(52) U.S. Cl. ..... Plt./152

(58) Field of Classification Search ..... Plt./152
See application file for complete search history.

(56) References Cited

OTHER PUBLICATIONS

Lin ye ke ji et al., "Forest Science & Technology", Jan. 1989, pp. 16-18, Baker Auxiliary Stacks SD1. L56, No. 2—1990.

Crane, H.L. et al., Nut Breeding, U.S. Department of Agriculture Yearbook, Jan. 1937, pp. 827-837.

Hemming, E. Sam, "Chinese Chestnut in Maryland", Jan. 1944, pp. 32-34, A.R. Northern Nut Growers Assoc.

Kim, Kap Duk et al., Studies on the Farmers Cultivating Chestnut Orchards in Korea and Its Financial Analysis, Jan. 1971, pp. 51-74, Bull. Seol. Nut. Univ.Fores., No. 8.

Snare, Lester, Chestnuts Production, Jan. 1996, pp. 422-427, NSW Agriculture, Agfact H3.1.50., hhtp://www.rirdc.gov.au/pub/handbook/chestnuts.pdf.

Harris, Hubert et al., Three Chinese Chestnuts: Au-Cropper, Au-Leadder, and Au-Homestead—Their History and Production, Mar. 1980, pp. 3-8, Agricultural Experiment Station Auburn University Circular 247.

*Primary Examiner*—Annette H Para
(74) *Attorney, Agent, or Firm*—Haverstock & Owens LLP

(57) ABSTRACT

The disease resistant 'AU Encore' seguin offers food availability for wildlife over an extended period. A single plant drops nuts for a 2–3 month period (September 27–November 30). Nut size varies with season and the average weight is between 2 and 3 grams. The plant does not bloom until mid-May, therefore late spring frosts do not damage the flowers. In most seasons, the 'AU Encore' seguin cultivar will have 2–3 flushes of vegetative growth. The nut quality is similar to the Chinese chestnut in that it is high in starch and sugar (40–42%) and low in fats. 'AU Encore' seguin is an excellent companion cultivar for 'AU Premier' seguin since the major nut drop for 'AU Encore' seguin occurs after the major nut drop period of 'AU Premier' seguin.

6 Drawing Sheets

Latin name of the genus and species of the plant claimed: *Castanea seguinii*.

Variety denomination: 'AU Encore'.

BACKGROUND OF THE INVENTION

A Chinese chestnut planting was established at Auburn University, Auburn, Ala., from nuts collected in Hubei Province, P.R. China. Plants were grown in containers under sprinkler irrigation at the main campus and selection were made for dwarfism, precocity, cold hardiness, everbearing, productivity, pest resistance, nut size and quality.

SUMMARY OF THE INVENTION

The present invention relates to a new and distinct sequin dwarf chestnut cultivar that is precocious, produces a heavy crop annually, begins nut drop about September 27 and continues nut drop through November 30. The small nut size (2.4 g) and continuous nut drop over an extended time makes the 'AU Encore' seguin an ideal high energy food for wildlife. The seguin nut size is ideal for consumption by quail and turkey. It produces nuts the year of establishment. The nuts are larger than most seguin chestnuts but not as large as Chinese chestnuts. The majority of the nuts from 'AU Encore' seguin drop after the majority of the nuts from 'AU Premier'

Seguin drop. The 'AU Premier' and the 'AU Encore' seguins are excellent companion cultivars as they both drop nuts over an extended period but the major nut drop period of the cultivars do not overlap. The plant is not affected by chestnut gall wasp, chestnut blight or leaf spot. 'AU Premier' is disclosed in U.S. patent application Ser. No. 12/012,092, filed on Jan. 30, 2008, and entitled "Chestnut plant named 'AU Premier'", which is hereby incorporated by reference.

The new cultivar is able to be asexually reproduced by budding or grafting onto a seguin seedling rootstock. The unique characteristics come true to form and are established and transmitted through succeeding asexual propagation.

DETAILED BOTANICAL DESCRIPTION

Figure 1:
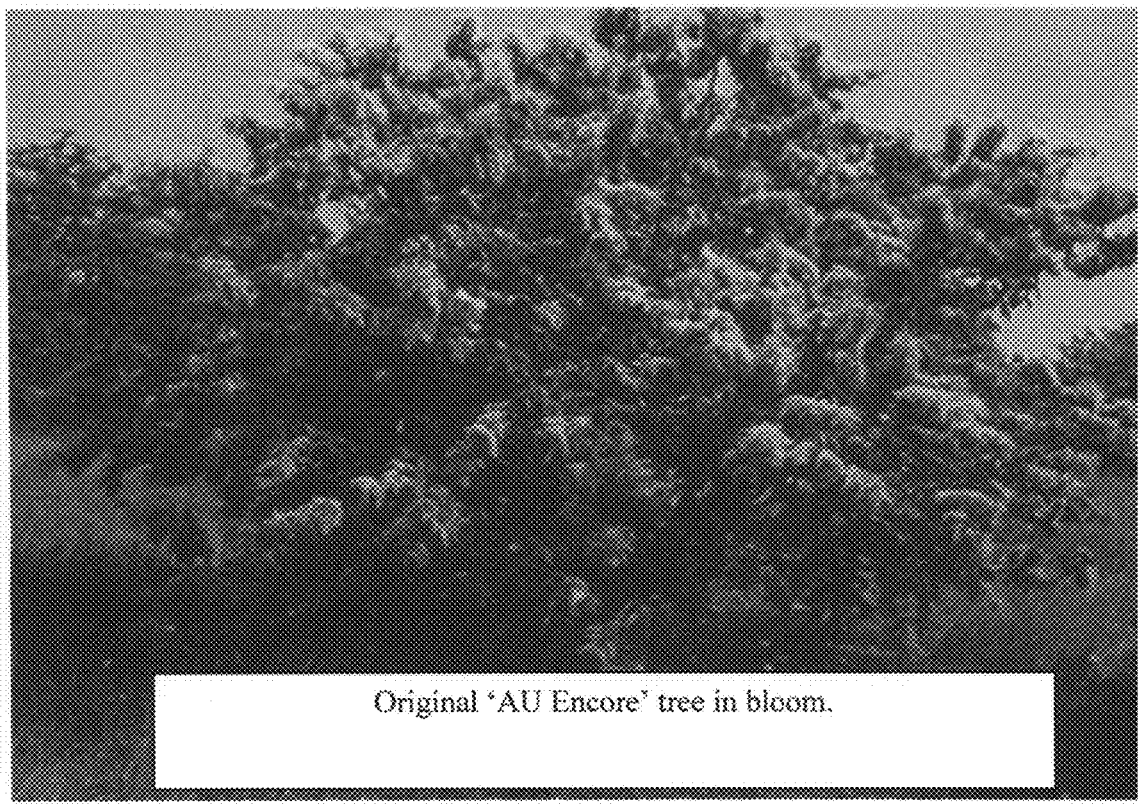
FIG. 1 is a photograph of a tree in bloom of the 'AU Encore' cultivar.
Figure 2:
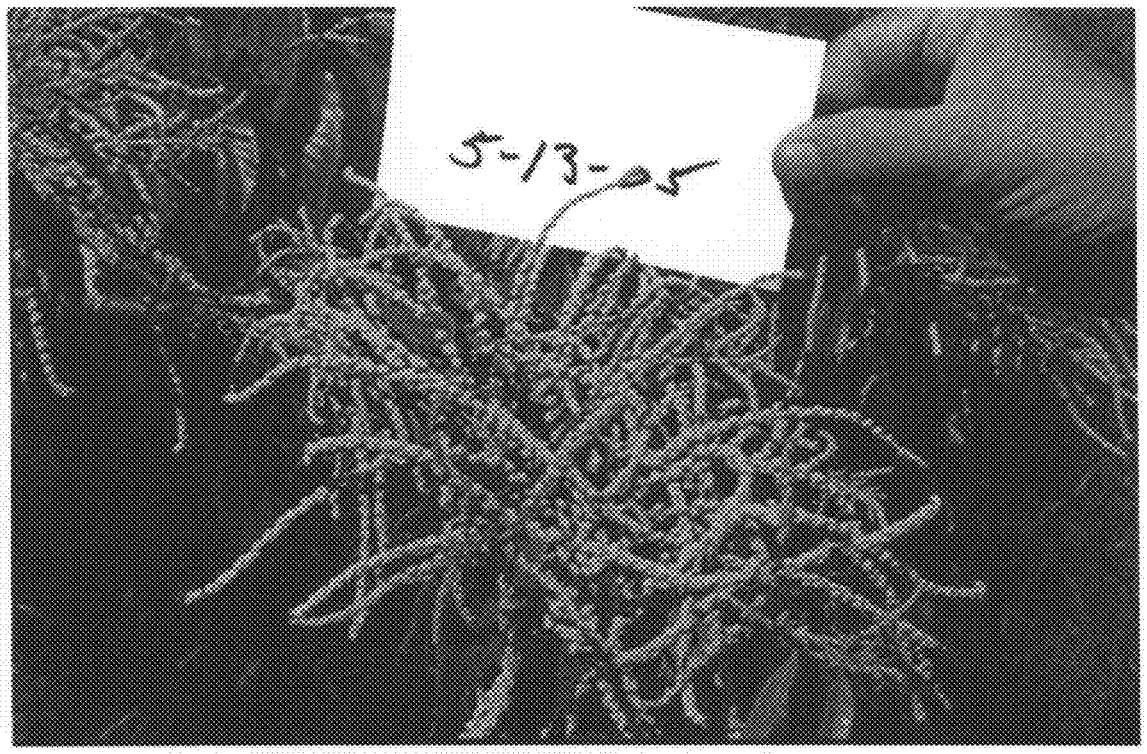
FIG. 2 is a photograph of a bloom on a shoot of the 'AU Encore' cultivar.
Figure 3:
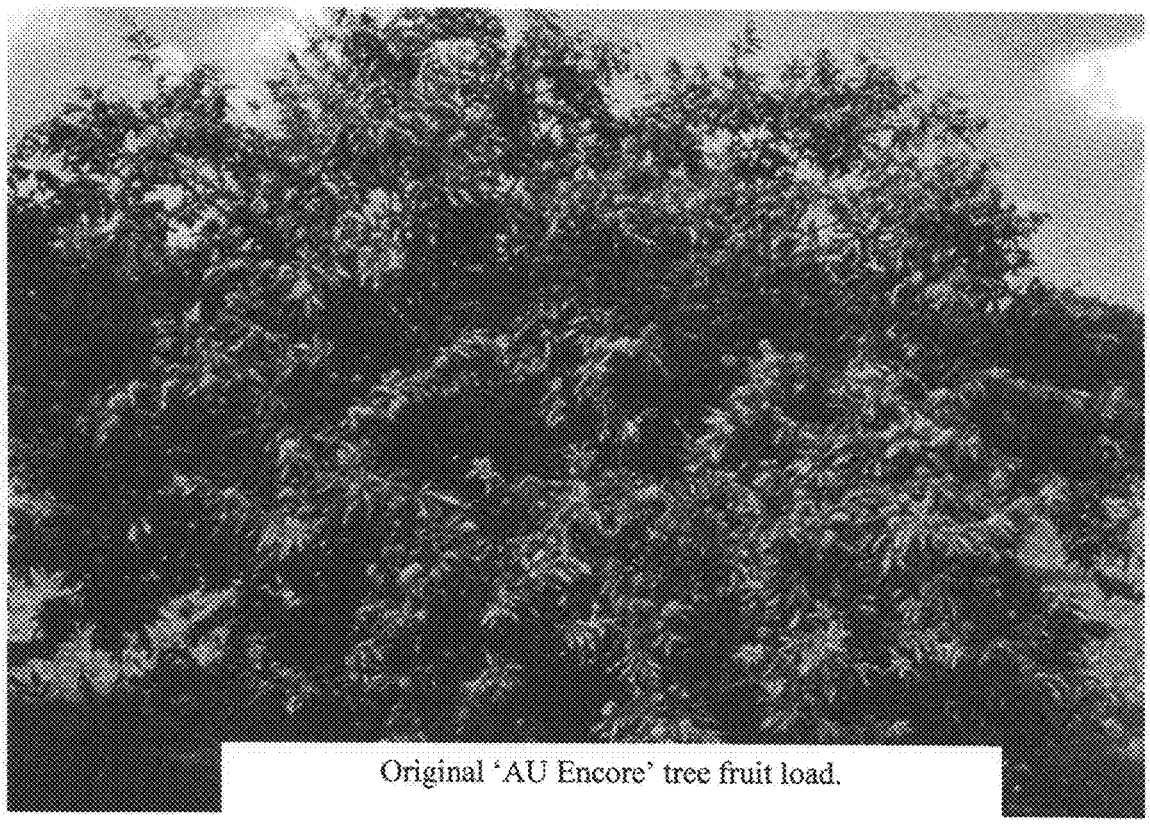
FIG. 3 is a photograph of a tree with fruit of the 'AU Encore' cultivar.
Figure 4:
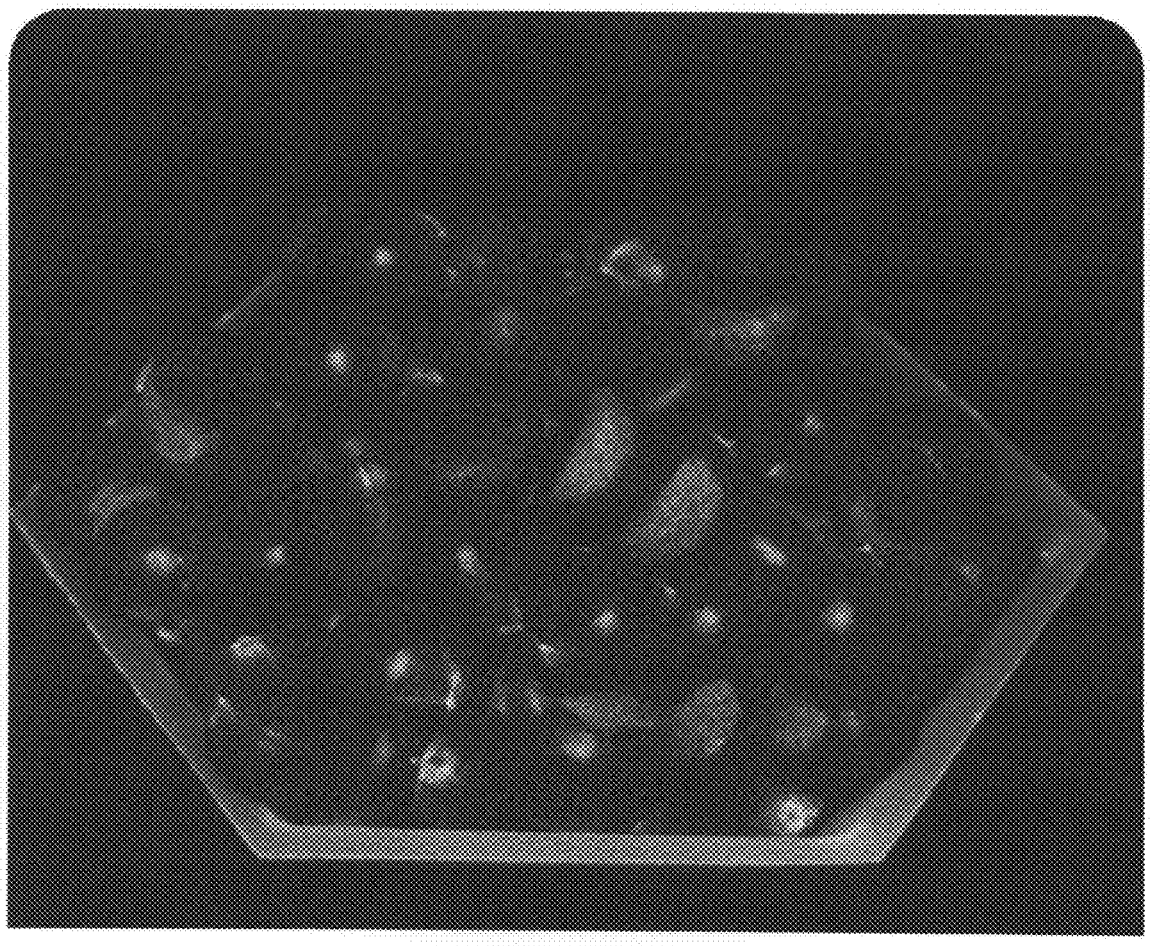
FIG. 4 is a photograph of nuts of the 'AU Encore' cultivar.
Figure 5:
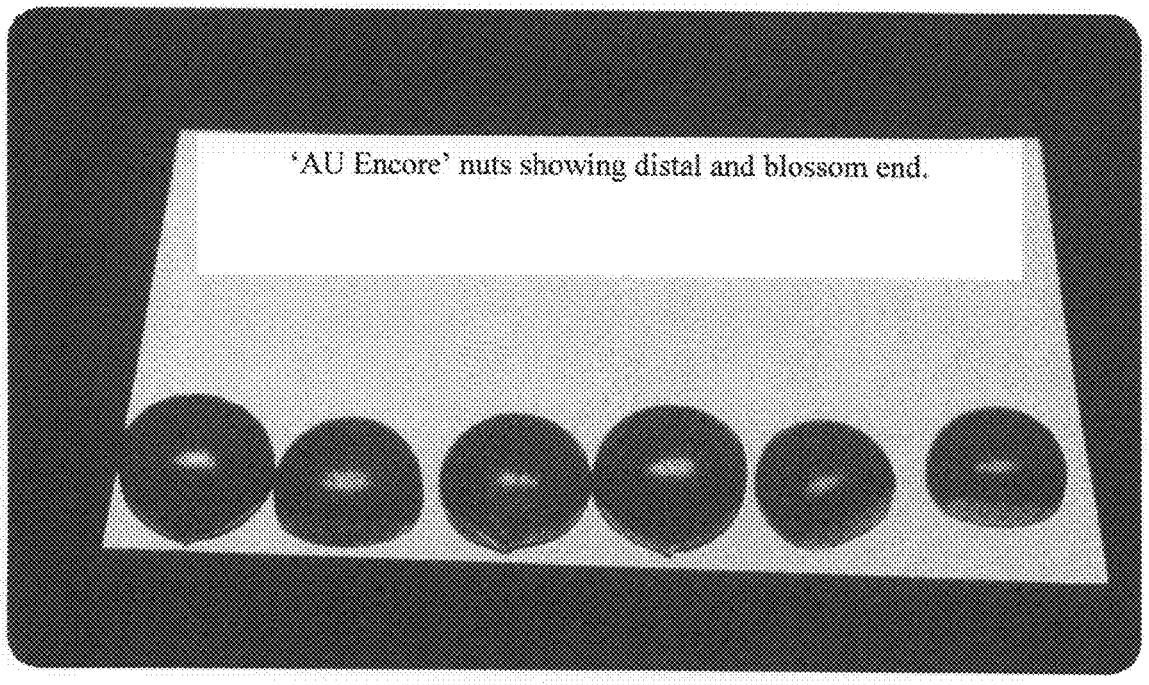
FIG. 5 is a photograph of nuts of the 'AU Encore' cultivar.
Figure 6:
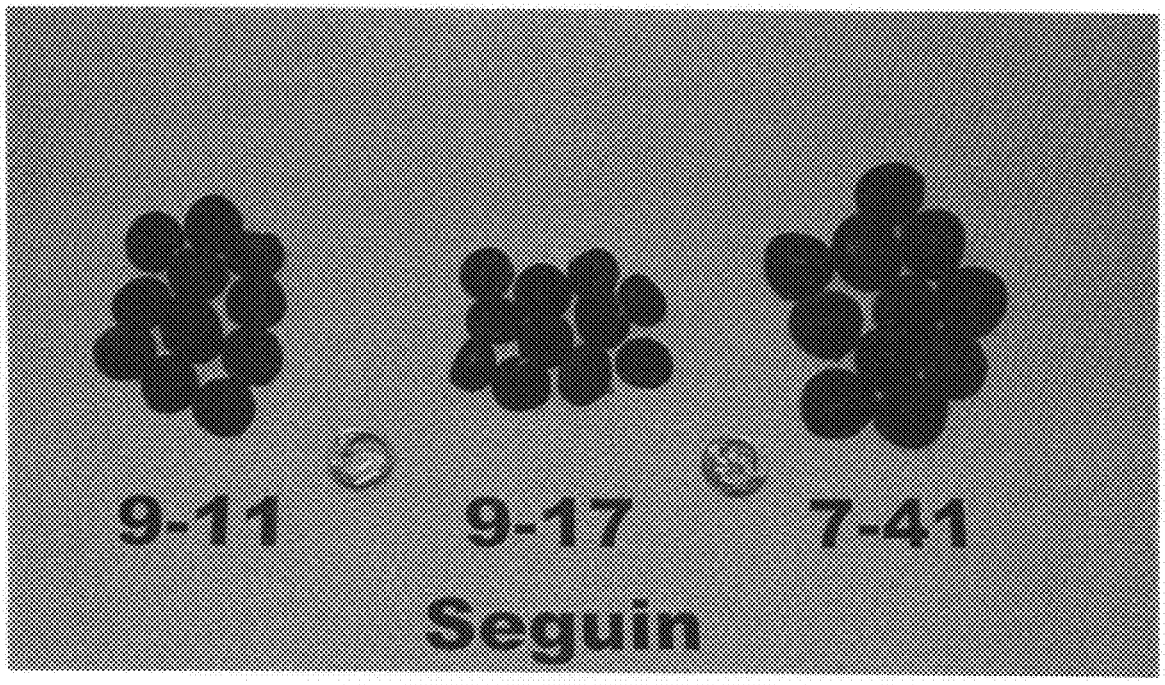
FIG. 6 is a photograph of nuts of the 'AU Premier' cultivar and the 'AU Encore' cultivar.

Seguin chestnut, also spelled "sequin," is one of two chestnut species, *Castanea mollissima* and *C. seguinii,* native to China. It grows as a bush or small tree and is commonly found throughout southeastern and central China. Seguin chestnut is a temperate species and its natural range extends from the Changjiang River region and southeastern China, northward to the southern Hubei province, southward to Guangdong province and westward to Sichuan and Guangxi provinces, a region whose climate is similar to that of the southeastern U.S.A. The plant bears three nuts per bur and the nut size is small (0.5–3 g). It has remained as a noncultivated species in China. The wildly grown nuts and wood are normally harvested by local farmers for food and fuel. The natural range of *C. sequinii* largely overlaps that of *C. mollissima* in southeastern and central China. Natural hybridization is able to occur and morphologically distinguishing *C. mollissima* from *seguinni* has proven difficult in natural forests. One leaf trait, pubescence on the underside of the leaves, has been studied and used for species identification. Scale-like glandular trichomes are able to be observed on the underside of seguin chestnut leaves with a 10x hand lens, while the underside of Chinese chestnut leaves are pubescent. Despite many efforts to use seguin as a dwarfing rootstock for commercial Chinese chestnut cultivars, it has not been successful due to the complete graft incompatibility between these two species.

Precocity. The plants normally flower at 2–15 months of age after seed germination. It is not unusual for plants to flower as early as three weeks. More than 90% of seedlings produced nuts in the first growing season in Alabama when seeds, introduced from China, were planted. Sprouts resulting from cold damage, pruning or other plant injury bear fruit the first year of development. Plants growing in containers that had the top portion of the plant killed during a snow storm had sprouts develop from the root system and produced a crop of nuts that year. In China, the species is subjected to yearly coppicing in most mountain areas for firewood on which local farmers depend as fuel. The cut off plants develop sprouts from the stump or root system when growth starts in the spring and produces a crop of nuts the same year. The 'AU Encore' cultivar produces nuts the first growing season and on multiple vegetative flushes each season and has not exhibited any signs of cold injury.

Everbearing. The continuous flowering throughout the growing season described as 'everbearing' is an important characteristic of the seguin chestnut. Twenty percent of plants of two populations collected in Hubei, China, developed bisexual catkins at each new node throughout the growing season. The remaining 80% of the plants were sequential flowering in that the plants produce a set of male and bisexual flowers, after an interval of vegetative growth, a set of flowers develop with each new flush of growth.

'AU Encore' is a sequential flowering cultivar. The first burs mature and start dropping nuts during the third to fourth week of September and nuts continue dropping through November. The first bloom occurs in mid-May each season.

The species is resistant to *Cryphonectria parasitica,* causal agent of chestnut blight. Seguin is generally considered less susceptible to the chestnut gall wasp (*Dryocosmus kuriphilus* Yasumatsu) than Chinese chestnut because of its growing and flowering habits. No gall wasp damage has been detected on 'AU Encore' or any other seguin selections in Auburn tests even though some Chinese chestnut cultivars growing in the same orchard exhibited gall wasp damage.

Some of the original seedlings had a leaf spot problem caused by *Colletotrichum gloeosporioides.* Infected and defoliated plants were discarded during the recurrent selection program. Leaf spot has not been observed on 'AU Encore.'

The table below illustrates the specific differences between the 'AU Encore' cultivar and the 'Revival' cultivar.

---

The botanical details of this new and distinctive variety of chestnut tree - with color definitions (except those in common color terms) referenced to Royal Horticultural Society's Colour Chart (RHS) and color was also determined using an electronic spectrophotometer to determine hue angle and chroma (spectrophotometer model CM-2002; Minolta Camera Co., Japan).

'AU ENCORE' CHESTNUT

Tree:

Size (at maturity) - small
Height 4.5 meters, canopy width 6.1 meters, canopy area 42 sq. meters
Vigor - vigorous Trunk:

Form -trunk upright, tree shape round; branches low and dense, spreading.
Texture - relatively smooth
Color of bark - Greyed-green, RHS 197A, Chroma C* 14.72, hue angle 85.04

Branches:

Form - strong
Texture - relatively smooth
Lenticels - few, small
Branching habit - low, dense and spreading.
Color - new wood: brown, RHS N200A, Chroma C* 12.15, hue angle 70.82; mature wood: greyed-green, RHS 197A, Chroma C*9.56, hue angle 90.16

Foliage:

Quantity - abundant
Density - dense

Leaves:

Size - small. Length (cm) 12.3 (10.5-14.5) [20]
width (cm) 5.2 (4.3-6.2) [20]
leaf ratio 2.4 (1.9-3.0) [20]
Shape - elliptic to oblong - elliptic
leaf tip- acuminate
leaf base- cuneate to rounded
Thickness- thin. Leaf venation 1° pinnate: 2°± parallel, not prominent abaxially
Texture - weakly coriaceous (thin)
Margin - coarsely serrate, ascending teeth
Petiole - length, short. (cm) 0.6(0.4-1.0) [20]
Petiole pubescence- glabrous
Color - adaxial surface, glabrous blade, occasionally sparse simple hairs on main veins. Medium green, moderately shiny, RHS 147A Chroma C* 13.30, hue angle 118.34
abaxial surface - small scale-like trichomes on blade, concentrated along midrib, sparse simple hairs on veins lighter to medium green, RHS 148A, Chroma C* 23.49, hue angle 97.56

Bloom:

Amount of bloom - heavy, at each node on current growth
Color - at anthesis, 161D greyed-yellow group, 157D green-white group, 155C white group
Blooming period - late, full bloom mid-May.
Age at which tree starts flowering - early, first year
Male flower - Catkin length (cm) - 7.8 (6.5-9.5) [15]
Male flower - stamen number per catkin - 13.2 (10-14) [13]
Female flower - flower number per bur - 3.0
Female flower - style number per flower 8.1 (7-9) [8]

Crop:

Bearing - annual, very precocious
Productivity - prolific
Ripening period - late September - late November
Distribution of nuts on tree - well distributed, chain of burs on -continued all new vegetative growth
Tenacity - burs open while on tree and nuts are easily released and fall.
Hull:

Description - spiny, round bur, average spine length 9.4 mm
Size - (mm) average length 43.7, width 25.5, depth 37.6
Number of nuts - normally 3 per bur
Dehiscence - splits easily and opens wide while still on tree and after nuts drop the bur is shed
Color - yellow-green at dehiscence, RHS N144C
Nut:

Size - small; average size (mm) - height 17.2, width 17.9; average weight 2.4 g, average number nuts per pound - 189.2
Form - usually 3 in a bur, flattened on 1 or 2 sides, hemispheric; often bulging sides appearing rounded distally.
Blossom end - little or no tip, distal ⅛ to ¼ end of nut, small fine white hairs exhibited.
Basal end - flattened
Color - light brown to red brown, RHS 200B, Chroma C* 14.07, hue angle 39.31
Shell - thin
Hardness of shell - relatively hard, yet not rigid
Texture of shell -smooth
Percentage of kernel to nut - high-95% shell out
Kernel:

Size - almost as large as nut size
Form - same as nut shape
Pellicle - thin brown
Flavor - excellent, very sweet
Color - greyed-yellow-RHS 162A, Chroma C* 52.05, hue angle 82.47
Resistance to insects: no insect susceptibilities noted due to bloom period and development, appears to be resistant to gall wasp damage
Resistance to disease: resistant to chestnut blight (*Cryphonectria parasitica*) and leaf spot (*Colletotrichum gloesporioides*)
The seguin tree and its nuts herein described may vary in slight detail due to climatic and soil conditions under which the variety may be grown; the present description being of the variety as grown in Camp Hill, Ala.

The botanical details of this new and distinct variety of chestnut tree - with color definitions (except those in common color terms) referenced to Maerz and Paul Dictionary of Color - are as follows:

'REVIVAL'

Tree:

Size (at maturity) - large
Vigor - very vigorous
Trunk:

Form - upright with branches spreading in upper reaches of tree.
Texture - relatively smooth
Color of bark - Silvergray (13-A-1)
Branches:

Form - strong
Texture - relatively smooth
Lenticels - few, small
Branching habit - spreading in upper region of tree
Color - new wood: reddish brown and glossy, mature wood: silver gray
Foliage:

Quantity - abundant
Density - dense
Leaves:

Size - large. Average length - 5-7" (including petiole).
Average width -2"
Shape - oblong with acute tip and rounded base
Thickness - thick
Texture - smooth
Margin - dentate
Petiole - length: medium. Thickness: medium.

-continued

Color - Top side - glossy dark green (22-L-12).
Under side - lighter green (21-D-7).
Bloom:

Amount of bloom - heavy
Color - cream white (17-B-1)
Blooming period - late. After leaf out in April
Age at which tree starts flowering - early; 2-3 years years after graft replacement.
Crop:

Bearing - regular (yearly) bearer
Productivity - prolific
Ripening period - short. September 15-October 1.
Distribution of nuts on tree - well distributed
Tenacity - burrs crack while on tree and nuts easily release, many falling by themselves
Hull:

Description - spiny, round burr
Size - 3-4" in diameter
Number of nuts - 2-3 per burr
Dehiscence - splits easily when still on tree. Some entire burrs split and fall to ground
Color - brown (15-A-8)
Nut:

Size - large. Average size - 1⅛" × 1⅛" × 1" thick.
Average weight - 24-32 nuts per pound
Form - broad and ovoid on one side, flat on other side
Blossom end - pointed tip
Basal end - flattened
Color - India Red (7-L-6).
Shell - thin
Hardness of shell - relatively hard, yet not rigid
Texture of shell - smooth
Percentage of kernel to nut - very high (95%)
Kernel:

Size - almost as large as nut size
Form - same as nut shape
Pellicle - thin
Flavor - excellent. Very sweet.
Color - Oyster white (10-B-1)
Resistance to insects: no unusual susceptibilities noted
Resistance to disease: very high inherent resistance to chestnut bark fungus (*Endothia parastica*), no other susceptibilities to any other disease
The chestnut tree and its nuts herein described may vary in slight detail due to climatic and soil conditions under which the variety may be grown; the present description being of the variety as grown in Alachua, Fla.

'AU Buck I' is different from 'AU Encore' in several ways. For example, the trees, the trunk colors, the branch colors, the leaves, the crop and the nuts have differences. Specifically, the 'AU Buck I' tree is taller with a canopy width and canopy area larger than the 'AU Encore' tree. The 'AU Buck I' has a grey-brown trunk, and the 'AU Encore' has a greyed-green trunk. The 'AU Buck I' branches are grey-brown; whereas, the 'AU Encore' branches are brown (new) or greyed-green (mature). The leaves differ in size, shape, thickness, texture, margin, petiole and color. The ripening period for the 'AU Buck I' is around August 28, but the 'AU Encore' ripening period is late September through late November. The average weight of the nuts of 'AU Buck I' is 9.3 grams versus 2.4 grams for 'AU Encore'. Furthermore, 'AU Buck I' has roughly 49 nuts per pound, and 'AU Encore' has roughly 189.2 nuts per pound.

'AU Buck II' is different from 'AU Encore' in several ways. For example, the trees, the trunk colors, the branch colors, the leaves, the crop and the nuts have differences. Specifically, the 'AU Buck II' tree is taller with a canopy width and canopy area larger than the 'AU Encore' tree. The 'AU Buck II' has a grey-brown trunk, and the 'AU Encore' has a greyed green trunk. The 'AU Buck II' branches are brown (new) or grey-brown (mature); whereas, the 'AU Encore' branches are brown (new) or greyed-green (mature). The leaves differ in size, shape, thickness, texture, margin, petiole and color. The ripening period for the 'AU Buck II' is around September 14, but the 'AU Encore' ripening period is late September through late November. The average weight of the nuts of 'AU Buck II' is 16.6 grams versus 2.4 grams for 'AU Encore'. Furthermore, 'AU Buck II' has roughly 27 nuts per pound, and 'AU Encore' has roughly 189.2 nuts per pound.

'AU Buck III' is different from 'AU Enore' in several ways. For example, the trees, the trunk colors, the branch colors, the leaves, the crop and the nuts have differences. Specifically, the 'AU Buck III' tree is taller with a canopy width larger than the 'AU Encore' tree. The 'AU Buck III' has a brown trunk, and the 'AU Encore' has a greyed-green trunk. The 'AU Buck III' branches are brown (new) or grey-brown (mature); whereas, the 'AU Encore' branches are brown (new) or greyed-green (mature). The leaves differ in size, thickness, texture, margin, petiole and color. The ripening period for the 'AU Buck III' is around September 25, but the 'AU Encore' ripening period is late September through late November. The average weight of the nuts of 'AU Buck III' is 10.9 grams versus 2.4 grams for 'AU Encore'. Furthermore, 'AU Buck III' has roughly 42 nuts per pound, and 'AU Encore' has roughly 189.2 nuts per pound.

'AU Buck IV' is different from 'AU Encore' in several ways. For example, the trees, the trunk colors, the branch colors, the leaves, the crop and the nuts have differences. Specifically, the 'AU Buck IV' tree is taller with a canopy area smaller than the 'AU Encore' tree. The 'AU Buck IV' has a brown trunk, and the 'AU Encore' has a greyed-green trunk. The 'AU Buck IV' branches are grey-brown (new) or greyed-green (mature); whereas, the 'AU Encore' branches are brown (new) or greyed-green (mature). The leaves differ in size, shape, thickness, texture, margin, petiole and color. The ripening period for the 'AU Buck IV' is around October 10, but the 'AU Encore' ripening period is late September through late November. The average weight of the nuts of 'AU Buck IV' is 15.5 grams versus 2.4 grams for 'AU Encore'. Furthermore, 'AU Buck IV' has roughly 29 nuts per pound, and 'AU Encore' has roughly 189.2 nuts per pound.

'AU Gobbler I' is different from 'Au Encore' in several ways. For example, the trees, the branches, the leaves, the crop and the nuts have differences. Specifically, the 'AU Gobbler I' tree is taller with a canopy width and a canopy area larger than the 'AU Encore' tree. The 'AU Gobbler I' branches are upright and high/diffuse; whereas, the 'AU Encore' branches are strong and low/dense/spreading. The leaves differ in size, shape, thickness, texture, margin and color. The ripening period for the 'AU Gobbler I' is around August 25 and continues for 4–5 weeks, but the 'AU Encore' ripening period is late September through late November. The average weight of the nuts of 'AU Gobbler I' is 7.7 grams versus 2.4 grams for 'AU Encore'. Furthermore, 'AU Gobbler I' has roughly 59 nuts per pound, and 'AU Encore' has roughly 189.2 nuts per pound.

'AU Gobbler II' is different from 'AU Encore' in several ways. For example, the trees, the branches, the leaves, the crop and the nuts have differences. Specifically, the 'AU Gobbler II' tree is taller with a canopy width and a canopy area larger than the 'AU Encore' tree. The 'AU Gobbler II' branches are spreading; whereas, the 'AU Encore' branches are strong. The leaves differ in size, shape, thickness, texture, margin and color. The ripening period for the 'AU Gobbler II' is around September 5 and continues for 4–5 weeks, but the 'AU Encore' ripening period is late September through late November. The average weight of the nuts of 'AU Gobbler II' is 5.7 grams versus 2.4 grams for 'AU Encore'. Furthermore, 'AU Gobbler II' has roughly 65–101 nuts per pound, and 'AU Encore' has roughly 189.2 nuts per pound.

What is claimed is:

1. A new and distinct cultivar of the species *Castanea seguinii* named 'AU Encore' as described and illustrated herein.

* * * * *

Original 'AU Encore' tree in bloom.

Original 'AU Encore' tree fruit load.

'AU Encore' nuts.

Comparison of 'AU Premier' (9-11) and 'AU Encore' (7-41) nuts.